United States Patent [19]
Carbone et al.

[11] Patent Number: 5,962,025
[45] Date of Patent: *Oct. 5, 1999

[54] METHOD FOR TREATMENT OF SYSTEMIC SCLEROSIS AND RELATED FIBROTIC DISEASES

[75] Inventors: Laura Carbone; Andrew H. Kang; Kevin McKown; Arnold E. Postlethwaite, all of Memphis, Tenn.; Jerome M. Seyer, Virginia Beach, Va.

[73] Assignee: The University of Tennessee Research Corporation, Knoxville, Tenn.

[*] Notice: This patent issued on a continued prosecution application filed under 37 CFR 1.53(d), and is subject to the twenty year patent term provisions of 35 U.S.C. 154(a)(2).

[21] Appl. No.: 08/682,021

[22] Filed: Jul. 16, 1996

[51] Int. Cl.$^6$ ..................................................... A61K 35/12
[52] U.S. Cl. .......................... 424/520; 424/572; 424/451; 424/464; 514/801; 530/356
[58] Field of Search ..................................... 424/520, 572, 424/451, 464; 514/801; 530/356

[56] References Cited

U.S. PATENT DOCUMENTS 4,444,752   4/1984   Prudden ...................................... 424/95
5,399,347   3/1995   Trentham et al. .................... 424/184.1

FOREIGN PATENT DOCUMENTS

PCT/US93/
  09113   9/1993   WIPO .

OTHER PUBLICATIONS

Wardale et al., Quantification and immunolocalisation of porcine articular and growth plate cartilage collagens, J. Cell Sci. 105:975–984, 1993.

Mosmann et al., The role of IL–10 in crossregulation of TH1 and TH2 responses, Immunology Today, 12:A49–A53, 1991.

Fiocco et al., Early phenotypic activation of circulating helper memory T cells in scleroderma: correlation with disease activity, Ann. Rheum. Dis., 52:272–277, 1993.

Dawnay et al., Microalbuminuria in systemic sclerosis, Ann. Rheum. Dis., 51:384–388, 1992.

Clements et al., Inter and intraobserver variability of total skin thickness score (Modified Rodnan TSS) in systemic sclerosis, J. Rheumatol., 22:1281–1285, 1995.

Clements et al., Health Assessment Questionnaire (HAQ) in patients with early, diffuese cutaneous systemic sclerosis (SSc), Arthritis and Rheumatism, 37(9)Suppl:S260, Abstract #603, 1994.

Dawnay et al., 1992, "Microalbuminuria in Systemic Sclerosis," Ann. Rheumatic Diseases 51:384–388.

Fiocco et al., 1993, "Early Phenotypic Activation of Circulating Helper Memory t Cells in Scleroderma: Correlation with Disease Activity," Ann. Rheumatic Diseases 52:272–277.

Mosmann et al., 1991, "The Role of IL–10 in Crossregulation of $T_H1$ and $T_H2$ Responses," Immunology Today 12:A49–A53.

Flick et al., 1988, "Esophageal Motor Abnormalities in Children and Adolescents with Scleroderma and Mixed Connective Tissue Disaeas", Pediatrics 82:107–111.

Garty et al., 1991, "Pulmonary Functions in Children with Progressive Systemic Sclerosis", Pediatrics 88:1161–1167.

Kagnoff, M.F., 1982, "Oral Tolerance", Ann. NY Acad. Sci. 392:248–265.

Lider et al., 1989, "Suppression of Experimental Autoimmune Encephalomyelitis by Oral Administration of Myelin Basic Protein", J. Immunol. 142:748–752.

Nagler–Anderson et al., 1986 "Suppression of Type II Colagen–induced Arthritis by Intragastric Administration of Soluble Type II Collagen", Proc. Natl. Acad. Sci. U.S.A. 83:7443–7446.

Nussenblatt et al., 1990, "Inhibition of S–Antigen Induced Experimental Autoimmune Uveoretinitis by Oral Induction of Tolerance with S–Antigen", J. Immunol. 144:1689–1695.

Pai et al., 1995, "Efficacy of Dexamethasone Pulse Therapy in Progressive Systemic Sclerosis", Int. J. Dermatol. 34(10):726–728.

Trentham et al., "Effects of Oral Administration of Type II Collagen on Rheumatoid Arthritis", 1993, Science 261:1727–1730.

Vallance et al., 1995, "Immunosuppressive Treatment of the Pulmonary Manifestations of Progressive Systemic Sclerosis",O Curr. Opin. Rheumatol. 7(3):174–182.

Weiner et al., 1993, "Double–blind Pilot Trial of Oral Tolerization with Myelin Antigens in Multiple Sclerosis", Science 259:1321–1324.

Wilson et al., 1995, J. Dermatol. 22(9):637–42.

Zhang et al., 1991, "Suppression of Diabetes in Nonobese Diabetic Mice by Oral Administration of Porcine Insulin", Proc. Natl. Acad. Sci. U.S.A. 88:10252–10256.

Primary Examiner—Michael G. Wityshyn
Assistant Examiner—Janet M. Kerr
Attorney, Agent, or Firm—Chernoff, Vilhauer, McClung & Stenzel, LLP; Howard Eisenberg, Esq.

[57] ABSTRACT

The present invention is directed to a method and pharmaceutical formulations for the treatment of systemic sclerosis in mammals, by oral administration of collagen, including type I collagen, or biologically active peptide fragments thereof.

8 Claims, No Drawings

METHOD FOR TREATMENT OF SYSTEMIC SCLEROSIS AND RELATED FIBROTIC DISEASES

The information disclosed in this Specification was made in part with Government support by grant no.AR-07317, awarded by the National Institute of Health. The government may have certain rights in the invention disclosed in this Specification.

1. FIELD OF THE INVENTION

This invention relates generally to treatments for systemic sclerosis and related fibrotic diseases. More specifically, the invention relates to the oral administration of collagen, preferably type I collagen, to treat systemic sclerosis and related fibrotic diseases.

2. BACKGROUND OF THE INVENTION

Systemic Sclerosis And Related Fibrotic Diseases. Systemic sclerosis, more commonly referred to as scleroderma, is an uncommon autoimmune disorder of unknown etiology. The disease state is characterized by widespread vascular injury, perivascular and tissue accumulation of CD4+ T cells and monocytes, and excessive extracellular matrix deposition in skin and internal organs. More particularly, manifestations of systemic sclerosis include lowered IL-10 production by peripheral blood mononuclear cells and $CD4^+$ $CD26^+$ levels. Improvement of systemic sclerosis has been traditionally measured by application of the Modified Rodnan Skin Score and Modified Health Assessment Questionnaire.

Related disease states, including primary and secondary Raynaud's phenomena, and the severity of such states can be identified by these same characteristics and measurements.

While systemic sclerosis has been long and widely studied, for example, as reported by Garty, et al., 1991, Pediatrics 88:1161–1167 and Flick, et al., 1988, Pediatrics 82:107–111, no viable treatment has been shown to alter the disease's pathogenetic mechanisms. Rather, the diverse experimental treatments disclosed in the literature to date, including dexamethasone pulse therapy (Pai, et al., 1995, Int. J. Dermatol. 34(10):726–728), the administration of tissue plasminogen activator (Wilson, et al., 1995, J. Dermatol. 22(9):637–42) and the use of immunosuppressive agents, such as cyclophosphamide (Vallance, et al., 1995, Curr. Opin. Rheumatol. 7(3):174–182), have resulted in mixed findings. Various regimens to treat one or more compromised functions resulting from the onset of systemic sclerosis (e.g. Garty, et al., supra, disclosing the administration of D-penicillamine to benefit pulmonary function) have similarly failed to result in any significant improvements.

Oral Tolerance. Oral tolerance is the phenomenon by which the feeding of antigen results in specific unresponsiveness to the same antigen administered parenterally. Kagnoff, 1982, Ann.NY Acad. Sci. 392:248–265. The feeding of putative autoantigens has produced cellular tolerance and improvement or the prevention of disease in a number of animal models or autoimmune illnesses and diseases which are mediated by T-cells. See generally, Zhang, et al., 1991, Proc. Natl. Acad. Sci. (USA) 88:10252–10256; Nagler-Anderson, et al., 1986, Proc. Natl. Acad. Sci. (USA) 83:7443–7446; Lider, et al., 1989 J. Immunol. 142:748–752; Nussenblatt, et al., 1990, 142:1689–1695. In humans, it has been reported that the oral administration of myelin basic protein and type II chick collagen have been helpful in treating multiple sclerosis and rheumatoid arthritis, respectively. Weiner, et al., 1993, Science 259:1321–1324; Trentham, et al., 1993, Science 261:1727–1730.

Although systemic sclerosis and oral tolerance effects have been studied continuously since at least the early 1970's, prior to the instant invention, the phenomenon of oral tolerance had not been applied to the treatment of systemic sclerosis.

3. SUMMARY OF THE INVENTION

Collagen is a primary component of the extracellular matrix and connective tissue. At present, approximately nineteen collagen types have been identified. Type I collagen is the primary collagen component of the dermis, lung, kidney, heart and intestine, all of which are commonly affected tissues in systemic sclerosis. Types III, V, VI, VII, XII and XIV collagen are also found in tissue affected by systemic sclerosis and related fibrotic diseases. Peripheral blood mononuclear cells (PBMC) from systemic sclerosis patients produce cytokines when cultured with type I collagen or constituent alpha chains of type I collagen.

The methods of the claimed invention are directed to the treatment of systemic sclerosis and related fibrotic diseases by the oral administration of collagen. Preferably, the administered collagen is type I collagen. Also preferably, the collagen is administered orally.

The present invention is further directed to compositions comprising collagen, and preferably type I collagen, wherein the collagen is formulated for administration to a patient in need.

4. DEFINITIONS

As used in this Specification, the term "collagen" shall mean collagen isolated from natural sources, collagen synthesized using available chemical synthesis techniques and polypeptides manufactured using recombinant technology, including the expression of recombinant collagen by a host cell. The term "collagen" shall further mean fragments, derivatives and other molecules which are capable of inducing oral tolerance in systemic sclerosis and related fibrotic diseases and are encoded by a nucleic acid sequence which can hybridize to the nucleic acid sequence encoding collagen under stringent hybridization conditions. More specifically, as used in this Specification, "collagen type" shall refer to collagen, as defined above, which is Types I, III, V, VI, VII, IX or IV, depending upon the roman numeral designation.

As used in this Specification, the term "oral tolerance" shall mean the mechanism by which feeding an antigen results in specific unresponsiveness to the same antigen when administered parenterally or alternatively, when arising systemically as a result of a disease state.

As used in this Specification, the phrase "stringent hybridization conditions," as used herein, refers to those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M Sodium pyrophosphate, 5×Denhardt's solution, sonicated salmon sperm DNA (50 g/ml), 0.1% SDS, and 10% dextran sulfate at 42° C., with washes at 42° C. in 0.2×SSC and 0.1% SDS.

5. DETAILED DESCRIPTION OF THE INVENTION

5.1. Treatment of Systemic Sclerosis By Administration of Collagen

Administration of Collagen to Treat Systemic Sclerosis and Related Fibrotic Diseases. The collagen molecules of the present invention can be administered to a patient in need, alone, or in pharmaceutical compositions where one or more of the molecules are mixed with suitable carriers or excipient(s) at doses to treat or ameliorates systemic sclerosis and related fibrotic disease.

Whether the composition is comprised of one collagen type (or fragment thereof) alone or a combination of collagen types or fragments as the active ingredient, such composition is prepared by combining, in a pharmaceutically acceptable carrier substance, the collagen and the other active ingredients.

A therapeutically effective dose further refers to that amount of the compound sufficient to result in amelioration of symptoms. Techniques for formulation and administration of the compounds of the instant application may be found in "Remington's Pharmaceutical Sciences," Mack Publishing Co., Easton, Pa., latest edition.

Composition/Formulation. The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active molecules into preparations which can be used pharmaceutically.

For example, for oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Effective Dosage. Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein. The exact formulation and dosage can be chosen by the individual physician in view of the patient's condition. See, e.g., Fingl et al., 1975, in "The Pharmacological Basis of Therapeutics", Ch. 1 p.1. Preferably, the dosage of collagen is between about 100 $\mu$g to about 500 $\mu$g a day.

Packaging. The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Suitable conditions indicated on the label may include treatment of disorders or diseases in which the administration of a compound of the present invention is desired to ameliorate either the disease or disorder or symptoms related to such disease or disorder.

Measuring Effectiveness of Systemic Sclerosis Treatment Regimens. PBMCs from systemic sclerosis patients react to native human type I collagen and the alpha-1(I) and alpha-2(I) chains of collagen in culture by producing IL-10, IFN$\alpha$, IL-2, IL-6, and lymphocyte-derived chemotactic factors for monocytes and by lymphocyte transformation, as measured by 3H-thymidine incorporation. It therefore appears that T cells play a major pathogenic role in systemic sclerosis. Systemic sclerosis patients have T-cell immunity to the collagen type I, and the constituent collagen type I alpha chains, and related collagen types, including collagen types III, V, VI, VII, XII and XIV). Thus, the effectiveness of a specific systemic sclerosis treatment regimen may be determined by measuring the changes in production of certain factors by a patient's PBMCs.

The effectiveness of treatment regimens may also be measured using established scoring tests, including the Modified Rodnan's Skin Score test, as described in Clements, et a;. 1993, J. Rheum. 20:1892–1896, and Modified Health Assessment Questionnaire (MHAQ), as generally described in Poole and Steen, 1992, Arthritis Care & Research 4:27–31.

6. EXAMPLES

Clinical Protocol. Twenty patients, having either limited or diffuse systemic sclerosis were recruited for treatment. These patients were selected on the basis of whether their PBMCs reacted with bovine type I collagen in vitro by producing IL-10 or IL-2 when cultured. A "positive" response was chosen to be the production of IL-10 or IL-2 by PBMC treated with bovine type I collagen that is 2× the production of IL-10 or IL-2 by untreated PBMC.

The bovine type I collagen was solubilized in 0.1 M acetic acid and aliquoted into individual 1.0 ml doses in sterile tubes. These aliquots were kept refrigerated prior to use and added to 4 to 6 ounces of cold orange juice prior to ingestion. Patients received 0.1 mg of solubilized bovine type I collagen daily for one month and then 0.5 mg of solubilized bovine type I collagen daily for five months.

Clinical efficacy was determined using the following measurements:

a. Skin thickness scores, as determined by Rodnan Method, as described in Clements, et al., 1993, J. Rheum. 20:1892–1896. Scores were obtained at 0, 1, 2, 3, 6 and 12 months.

b. Pulmonary spirometry (PFT) with carbon monoxide diffusing capacity, as measured at 0, 3, 6 and 12 months.

c. Serum creatinine, as measured at 0, 1, 3, 6 and 12 months.

d. MHAQ, as described in Masi, et al., 1980, Arth. Rheum. 23:581–590.

Clinical improvement was defined as improvement in skin thickness score of 3, 10% improvement of DLCO or vital capacity or a a 25% improvement in creatinine.

Clinical Results. Systemic sclerosis patients administered collagen type I completing the above treatment regimen showed clinical improvement over time, as follows:

IL-10 Production Levels By PBMC. Administration of 0.1 mg/day of collagen type I for one month, increased to 0.5 mg/day for additional months was associated with a decrease in cellular immunity to human alpha-1(I) and alpha-2(I) collagen, as assessed by IL-10 production by PBMC.

More specifically, PBMC were taken from the tested patients and cultured in the presence of the alpha-1(I) or the alpha-2(I) chains of collagen type I, for 5 days and culture supernatants were quantitated for IL-10 by ELISA. Some patients were given NSAIDS, anonsteroidal anti-inflammatory drug, and these patients showed no decrease in IL-10 production. NSAIDS are known to interfere with oral tolerance induction. Loius, et al., 1996, Int. Arch Allegrgy Immunol. 109:21–26. The decrease in production of IL-10 by PBMC was from patients administered type I collagen alone.

Flow Cytometry Results. In the five patients in which flow cytometry used to measure T-cell subsets, after six months, as set forth in Table 1, patients showed significant decreases in the $CD4^+$ $CD26^+$ subset, suggesting that treatment of systemic sclerosis with collagen type I decreases the level of IL-2 producing T-cells.

TABLE 1

CD4+ CD26+ Levels In Patients
At 0 and 6 Months Treatment With Bovine Type I Collagen

| Number of Systemic | Mean CD4+ CD26+ Levels | |
|---|---|---|
| Sclerosis Patients | 0 months | 6 months |
| 5 | 94.8 ± 13.89 | 48.6 ± 14.46 | p = 0.025, wherein p = probability

Modified Rodnan Skin Score and MHAQ. Eleven patients completing six months of oral type I collagen treatment had improved Modified Rodnan Skin Scores and MHAQ scores, as set forth at Table 2.

TABLE 2

Clinical Parameters Scores
For Systemic Sclerosis Patients Treated With Type I Collagen

| Condition | Month | Value | p value (paired student's test) | n (# of patients treated) |
|---|---|---|---|---|
| Modified Rodnan Skin Score | 0 | 29.36 ± 359 | | 11 |
| Modified Rodnan Skin Score | 6 | 21.45 ± 4.45 | 0.02 | |
| MHAQ | 0 | 17.36 ± 3.28 | | 11 |
| MHAQ | 6 | 12.09 ± 2.33 | 0.02 | |

The present invention is not to be limited in scope by the exemplified embodiments which are intended as illustrations of single aspects of the invention, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

All references cited within the body of the instant specification are hereby incorporated by reference in their entirety.

We claim:

1. A method for treating systemic sclerosis in a patient in need of said treatment comprising administering orally or by inhalation a composition consisting essentially of a therapeutically effective amount of a collagen to said patient and inducing tolerance to the collagen.

2. The method of claim 1 wherein said therapeutically effective amount is from about 100 µg/day to about 500 µg/day.

3. The method of claim 1 wherein the collagen is a collagen type I.

4. The method of claim 1, wherein the composition further comprises a pharmaceutically acceptable carrier.

5. The method of claim 1 wherein the composition is administered orally.

6. The method of claim 5 wherein the administration is by a tablet, pill, dragee, capsule, liquid, gel, syrup, slurry, or suspension.

7. The method of claim 1 wherein the collagen is of a Type selected from the group consisting of I, III, IV, V, VI, VII, and IX.

8. The method of claim 1 which further comprises decreasing the patient's $CD4^+$ $CD26^+$ T-cell subset.

* * * * *